(12) United States Patent
Gottlieb et al.

(10) Patent No.: US 10,226,365 B2
(45) Date of Patent: Mar. 12, 2019

(54) PROSTHESIS SOCKET

(71) Applicant: OTTO BOCK HEALTHCARE GMBH, Duderstadt (DE)

(72) Inventors: Harald Gottlieb, Jutzenbach (DE); Jens Volkmar, Duderstadt OT Gerblingerode (DE); Andreas Leiniger, Leinefelde OT Birkungen (DE); Marco Volkmar, Duderstadt (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 0 days.

(21) Appl. No.: 14/355,482

(22) PCT Filed: Oct. 30, 2012

(86) PCT No.: PCT/EP2012/004536
§ 371 (c)(1),
(2) Date: Apr. 30, 2014

(87) PCT Pub. No.: WO2013/064240
PCT Pub. Date: May 10, 2013

(65) Prior Publication Data
US 2014/0288668 A1      Sep. 25, 2014

(30) Foreign Application Priority Data
Nov. 3, 2011  (DE) .................. 10 2011 117 801

(51) Int. Cl.
*A61F 2/80*       (2006.01)
*A61F 2/78*       (2006.01)
(Continued)

(52) U.S. Cl.
CPC .............. *A61F 2/80* (2013.01); *A61F 2/7812* (2013.01); *A61F 2/76* (2013.01);
(Continued)

(58) Field of Classification Search
CPC ........................................................ A61F 2/80
See application file for complete search history.

(56) References Cited

U.S. PATENT DOCUMENTS 5,246,464 A      9/1993  Sabolich
5,393,303 A *    2/1995  Shiono .................. A61F 5/0111
                                                  602/23
(Continued)

FOREIGN PATENT DOCUMENTS

DE            824 678 C    * 11/1951    ............... A61F 2/80
DE   102006046927 A1    4/2008
(Continued)

OTHER PUBLICATIONS

Computer generated translation of FR 2 828 093 A1, published on Feb. 7, 2003.*
(Continued)

*Primary Examiner* — David H Willse
(74) *Attorney, Agent, or Firm* — Holland & Hart

(57) ABSTRACT

A prosthesis socket for a prosthesis, which comprises a connecting member for a distal prosthesis device and an outer socket, which is made predominantly from a rigid material, and a proximal opening for receiving a residual limb and which is surrounded by an outer socket edge. The outer socket edge is made of a flexible and non-elastic material in a ventral region, the flexible and non-elastic material being adapted to the body shape of the wearer of the prosthesis socket.

16 Claims, 5 Drawing Sheets

(51) Int. Cl.
    *A61F 2/50*  (2006.01)
    *A61F 2/76*  (2006.01)
    *A61F 2/60*  (2006.01)

(52) U.S. Cl.
    CPC .............. *A61F 2002/5007* (2013.01); *A61F 2002/5053* (2013.01); *A61F 2002/5055* (2013.01); *A61F 2002/608* (2013.01); *A61F 2002/7818* (2013.01)

(56) References Cited

U.S. PATENT DOCUMENTS

| | | |
|---|---|---|
| 5,653,766 A | 8/1997 | Naser |
| 5,800,565 A | 9/1998 | Biedermann |
| 6,402,789 B1 * | 6/2002 | Gramnas ..................... 623/38 |
| 2004/0158332 A1 | 8/2004 | Carstens |
| 2007/0225824 A1 * | 9/2007 | Einarsson ................ A61F 2/78 623/36 |
| 2007/0276510 A1 | 11/2007 | Becker et al. |
| 2010/0042227 A1 | 2/2010 | Schmidt |
| 2010/0115757 A1 | 5/2010 | Sacherer |
| 2010/0191348 A1 | 7/2010 | Kettwig et al. |

FOREIGN PATENT DOCUMENTS

| | | | | |
|---|---|---|---|---|
| DE | 102006046928 A1 | 4/2008 | | |
| DE | 102007005648 A1 | 8/2008 | | |
| DE | 102007035410 A1 | 2/2009 | | |
| EP | 0760640 B1 | 8/1998 | | |
| EP | 1854621 A1 | 11/2007 | | |
| FR | 2 828 093 A1 * | 2/2003 | ............... | A61F 2/80 |
| GB | 515970 * | 12/1939 | ............... | A61F 2/80 |
| GB | 1 557 339 * | 12/1979 | ............... | A61F 2/80 |
| SU | 1685427 A1 * | 10/1991 | ............... | A61F 2/80 |

OTHER PUBLICATIONS

SU 1685427 A1, published on Oct. 23, 1991: human generated English translation.*
Wikipedia article on aramid, printed on Oct. 25, 2016.*
Wikipedia article on carbon fibers, printed on Oct. 25, 2016.*
Wikipedia article on fiberglass, printed on Oct. 25, 2016.*
PCT International Search Report for PCT International Patent Application No. PCT/EP2012/004536, dated Feb. 6, 2013.
European Office Action for Application No. 12788117.5, dated Oct. 29, 2015, 4 pages.

\* cited by examiner

PROSTHESIS SOCKET

TECHNICAL FIELD

The invention relates to a prosthesis socket for a prosthesis, said prosthesis socket having attachment means for a distal prosthetic device, and an outer socket which is formed mainly from a rigid material and comprises a proximal opening for receiving an amputation stump, said proximal opening being surrounded by an outer-socket edge.

BACKGROUND

Prosthesis sockets of this kind have long been known in the prior art and are used particularly with leg prostheses, for example in cases of above-knee amputation of the patient.

In known prosthesis sockets, the outer socket is, for example, made entirely of a fiber-reinforced plastic, for example a carbon-fiber-reinforced or glass-fiber-reinforced plastic. These materials are easy to work and are stable, and yet have a very low weight. In this way, it is possible to obtain a particularly light prosthesis or a particularly light prosthesis socket which nevertheless has good stability properties. In particular, the high degree of inherent stability of the outer socket gives the person wearing the prosthesis a feeling of security. The high degree of stability and strength of the outer socket also permits secure and stable attachment of distal prosthetic devices, for example a prosthetic foot, or a knee joint with an attached prosthetic lower leg and foot.

However, a disadvantage is that an amputation stump located in a prosthesis socket of this kind is largely or even completely shielded from perceptions of the environment. For example, when a person wearing a prosthesis fitted with a prosthesis socket of the type in question sits down and places his arms on his thighs, the rigid outer socket of the prosthesis socket does not allow him any possibility of corresponding feedback from his amputation stump. This therefore creates an unnatural and artificial sensation which greatly reduces the wearing comfort of a prosthesis fitted with such a prosthesis socket.

EP 0 760 640 B1 therefore discloses a prosthesis socket in which the outer socket is simply designed in the form of a receiving shell in which the distal end of the amputation stump is fitted. Starting from this receiving shell, three socket fingers extend to the proximal end of the prosthesis socket. These socket fingers are produced from a rigid and durable material and have a hook-and-loop fastening means on the inside face, i.e. the face directed toward the amputation stump. An inner socket, which is pulled on over the amputation stump itself, likewise has hook-and-loop fastening means at corresponding locations. The outer socket is secured on the inner socket through the cooperation of the hook-and-loop fastening elements on the inner socket and on the inside face of the outer socket. However, one disadvantage is that, by using hook-and-loop fastening means, relative movements can occur between the inner socket and the outer socket, particularly in the swing phase of a walking movement. Another disadvantage is that there is relatively little support particularly in the proximal region of the prosthesis socket, since the rigid outer socket does not extend into this region. The patient may therefore feel he has insufficient control over the prosthesis, which leads to increased instability and, consequently, to reduced wearing comfort.

U.S. Pat. No. 5,246,464 discloses a prosthesis socket with a rigid outer socket which is interrupted at some places. The outer socket nonetheless has an outer-socket edge which runs round the entire circumference of the amputation stump and defines the proximal end or proximal edge of the outer socket. As a result of the gaps provided in the rigid and fixed outer socket, an amputation stump located in the prosthesis socket is able to perceive the environment at least to a limited extent. In particular, objects lying on the amputation stump, or other parts of the patient's body supported on the amputation stump, for example the elbows, can be perceived inside these windows which are provided in the outer socket. However, since an outer socket of this kind has an outer-socket edge running all the way round the circumference, pressure sores and cuts can often occur here, which can lead to painful wounds.

The prior art therefore also discloses prosthesis sockets which have a rigid outer socket, but in which the outer-socket edge, which delimits the proximal opening of the outer socket, is formed at least partially by straps. Since these straps are responsible, at least in these regions of the outer socket edge, for the stability of the outer socket itself and for the secure arrangement of the prosthesis socket on the amputation stump, said straps have to be pulled relatively tight. This causes increased pressure on the amputation stump compared, for example, to an outer socket made entirely of a rigid material. This increased pressure on the amputation stump in the region of the straps can be very unpleasant for the wearer and may even become painful and lead to pressure sores and wounds.

SUMMARY

The object of the invention is therefore to propose a prosthesis socket which permits improved perception of the environment through the amputation stump and which at the same time ensures a secure hold on the amputation stump, does not lead to pressure sores during various movements, and does not adversely affect controllability.

The object is achieved, according to the invention, by a prosthesis socket of the type in question which is characterized in that the outer-socket edge is formed from the flexible and non-elastic material in a ventral region, wherein the flexible and non-elastic material is adapted to a body shape of the wearer of the prosthesis socket. The flexible and non-elastic material is preferably a fiber-reinforced plastic, which in particular comprises Dyneema fibers.

Materials of this kind, in particular Dyneema-reinforced plastic, are freely shapeable in a first, unhardened state. They can in particular be adapted to the body shape of the subsequent wearer of the prosthesis socket or of the prosthesis. In the context of the present invention, adaptation of the material to the body shape of the wearer of the prosthesis socket does not necessarily mean individual adaptation to every single wearer of the prosthesis or of the prosthesis socket. Instead, the chosen wording also covers a merely standardized adaptation of the flexible and non-elastic material to an expected body shape of the wearer. For example, this can include turning the outer socket edge out in order to alleviate potential pressure sores and prevent wounds. Such an adaptation cannot be achieved when the socket edge is formed at least partially by straps.

After the flexible and non-elastic material has been formed according to the expected body shape of the wearer of the prosthesis socket, this shape forms the rest position of the flexible and non-elastic material. This means that the material returns to this position when not subjected to other forces. However, because of the special properties of the material, in particular of the plastic reinforced with Dyneema fibers, the material has also preserved a residual flexibility in the hardened state, such that flexible deformations can take place under the effect of the loads that customarily occur when wearing a prosthesis socket of the present type. At the same time, however, the material is non-elastic, such that the proximal opening of the prosthesis socket, for example, cannot widen when a particular load is placed on the flexible and non-elastic material. In this way, a secure hold of the prosthesis socket on the amputation stump of the wearer of the prosthesis socket is ensured.

If a prosthesis socket according to the invention is used, for example, for the prosthesis of a patient whose leg has had to be amputated above the knee, increased loads occur in particular in the area of the outer-socket edge. In this area, prosthesis sockets from the prior art thus cause pressure sores on the amputation stump and, possibly, painful wounds. By contrast, in the design according to the invention, the flexible and non-elastic material of the outer socket, in the area of the outer-socket edge, is also flexible enough to change its shape as a result of the loads that occur in this case. The danger of pressure sores, or of wounds caused by chafing, is greatly reduced in this way.

By virtue of the flexibility of the material used in this area of the outer socket, it is at the same time possible for the wearer of the prosthesis socket, or of a prosthesis equipped therewith, to perceive influences of the environment, for example objects or body parts placed on the prosthesis socket, and thus to develop a more natural feel for the prosthesis. The wearing comfort of the prosthesis and of the prosthesis socket thus increases, thereby permitting a more natural relationship to the prosthesis.

The flexible and non-elastic material used is preferably a plastic reinforced with Dyneema fibers. Dyneema fibers are high-stretch polyethylene fibers. Comparable fibers are available on the market, for example under the brand name "Spectra". Fibers of this kind, and plastic reinforced with them, are particularly easy to work and have all the required properties. Alternatively, it is also possible to use polyamide fibers, for example Kevlar. It is not necessary that the fibers are coated across the whole surface area with a plastic or impregnated with the latter or embedded therein. However, in the edge regions of the surfaces formed by the fibers, i.e. the surfaces that are formed by the flexible and non-elastic material, the use of a plastic of this kind is advantageous, since this permits simple binding to the rigid material of the outer socket.

In a preferred embodiment, the rigid material of the outer socket is likewise a fiber-reinforced plastic. The latter is advantageously a glass-fiber-reinforced or carbon-fiber-reinforced plastic. These materials have the aforementioned advantages of having a low weight, having a high degree of stability and being easy to work. The controllability of the prosthesis is maintained by virtue of the high degree of inherent stability of the outer socket, a rigid support being advantageous for control particularly in the case of an above-knee socket.

In a particularly advantageous embodiment, the same plastic can be used for the rigid material and the flexible non-elastic material. In this way, one mold provided for this purpose can be fitted out in one working step with the respective fiber-reinforced plastic in the respective areas. In addition, the two fiber-reinforced plastics can harden at the same time and thus form a particularly strong, in particular materially cohesive bond. This results in increased stability, particularly in the contact area of the two fiber-reinforced plastics on the prosthesis socket. The useful life of the prosthesis socket is thus prolonged. Moreover, between the two adjoining materials, there is no interface, not even a shoulder, that would greatly reduce the wearing comfort of such a prosthesis socket.

The outer-socket edge is preferably formed from the flexible and non-elastic material in a dorsal region. Particularly in patients who have had to have a leg amputated above the knee, the dorsal region, i.e. the rear region, of the outer-socket edge is the region that is loaded most when sitting down while wearing the prosthesis with the described prosthesis socket. The patient in practice sits on the outer-socket edge. If the latter is rigid, stable and hard, this also causes unpleasant pressure here, which can lead to pressure sores or, as a result of chafing, even to wounds. These problems can be prevented by also using a flexible and non-elastic material in the dorsal region. When the patient sits down on the outer-socket edge, the flexible and non-elastic material deforms on account of its flexibility, such that it can adopt the shape best suited to the prevailing loads, and therefore pressure sores are reliably prevented.

It has proven particularly advantageous if the flexible and non-elastic material in the dorsal region of the outer-socket edge is the same material as the flexible and non-elastic material in the ventral region of the outer socket edge. If the two materials are also a fiber-reinforced plastic, in particular a plastic reinforced with Dyneema fibers, this fiber-reinforced plastic can again be the same as the plastic used for the rest of the outer socket which is formed from the rigid material. Therefore, the same advantages as have already been described are once again afforded here, namely a particularly strong, materially cohesive connection and a particularly smooth inside face of the outer socket, since steps and shoulders between two adjoining materials are reliably prevented.

The outer socket is advantageously interrupted at least one place. Such gaps or windows reduce the weight of the outer socket and also allow the wearer of the prosthesis socket and of the prosthesis the possibility of perceiving environmental influences in this area. It is conceivable that the gaps or windows are completely filled with the flexible and non-elastic material. As an alternative to this, it is also possible not to provide any material in these gaps; since the prosthesis socket of the prosthesis has an outer socket that is rigid over wide areas, it is advantageous if a cushioning layer is provided between the rigid outer socket and the amputation stump. For example, this cushioning layer can be pulled in the form of a liner or sleeve over the amputation stump. However, it has proven particularly advantageous if an inner socket made of a flexible material is arranged inside the outer socket. This can be a silicone socket, for example, which advantageously has an anti-adhesion coating in the proximal region, for example by means of CVD methods. This makes it much easier for the patient to step into the inner socket, because the static friction of the inner socket on the amputation stump is greatly reduced in this area. Such an inner socket can, for example, comprise two layers of HTV silicone. Inner sockets of this kind can be equipped with thickened cushioning regions or, at places requiring particular cushioning, with adhesive cushioning pads, for example. If appropriate, these can be produced, adapted and arranged individually for each patient. The elasticity of the silicone is preferably minimized in the area of the windows. This is ideally achieved by incorporating woven fabric into the silicone layers. The proximal edges of the inner socket remain elastically deformable.

An inner socket preferably comprises an integrated buckle which is arranged at the distal end and which can be produced from a flexible material, for example a fiber-reinforced plastic. This buckle prevents collapse or implosion of the inner socket and at the same time provides hold and stability for a valve attachment piece of a valve through which, if appropriate using a separate pump, an underpressure is produced between the inner socket and the amputation stump and holds the inner socket on the amputation stump.

If the windows or gaps in the outer socket of the prosthesis socket are filled with the flexible and non-elastic material, it is still possible for the wearer of the prosthesis socket to perceive environmental influences here. At the same time, however, it is possible to reliably prevent a situation where parts of the amputation stump bulge out from these gaps and windows, particularly when the foot is set down when wearing such a prosthesis. A so-called milking effect is also prevented in this way, and the wearing comfort of the prosthesis is further increased.

It is also advantageous if the inner socket is connected to the outer socket in a manner free of pistoning. In a particularly advantageous embodiment, this is achieved by at least one screw connection, in particular a distal screw connection, with which the inner socket is connected to the outer socket. The inner socket is preferably connected distally to the outer socket, in particular by screwing.

In connection systems known from the prior art, for example hook-and-loop fasteners, it is conceivable that, particularly in the swing phase of a leg prosthesis, the tensile forces acting on the prosthesis cause a relative movement to take place between the outer socket secured on the distal prosthetic device and the inner socket lying securely on the amputation stump. For the person wearing the prosthesis, a relative movement of this kind makes it feel as if the prosthesis is fitted loosely and not fully functionally on the amputation stump. A relative movement of this kind between the outer socket and the inner socket thus results in a feeling of considerable instability, which is reliably prevented by means of the inner socket being secured on the outer socket in a manner particularly free of pistoning.

In a preferred embodiment, it is possible for the flexible and non-elastic material to be designed in two parts which can be connected to each other by, for example, a hook-and-loop fastener or by a strap secured on the outside. In this way, the advantages of the flexible and non-elastic material, which is adapted to the body shape of the wearer, can be combined with the advantages of adjustability via a strap system or other kind of fastening mechanism. In this way, it is possible in particular for a patient to use the prosthesis socket over a long period of time, for example even if the volume of the amputation stump changes over the years. Individual adjustment of the size of the prosthesis socket is in this way possible to a limited extent.

The size of the ventral region, in which the outer socket is made from the flexible and non-elastic material, can vary considerably both in the circumferential direction and also in an extent from the proximal opening to the distal end of the prosthesis socket. It is thus possible, in this direction, to limit the extent of the ventral region to a few centimeters. As an alternative to this, an area with the flexible and non-elastic material can also be provided which extends over more than half of the extent of the outer socket in this direction.

BRIEF DESCRIPTION OF THE DRAWINGS

An illustrative embodiment of the present invention is explained in more detail below with reference to a drawing, in which.

DETAILED DESCRIPTION

Figure 1:
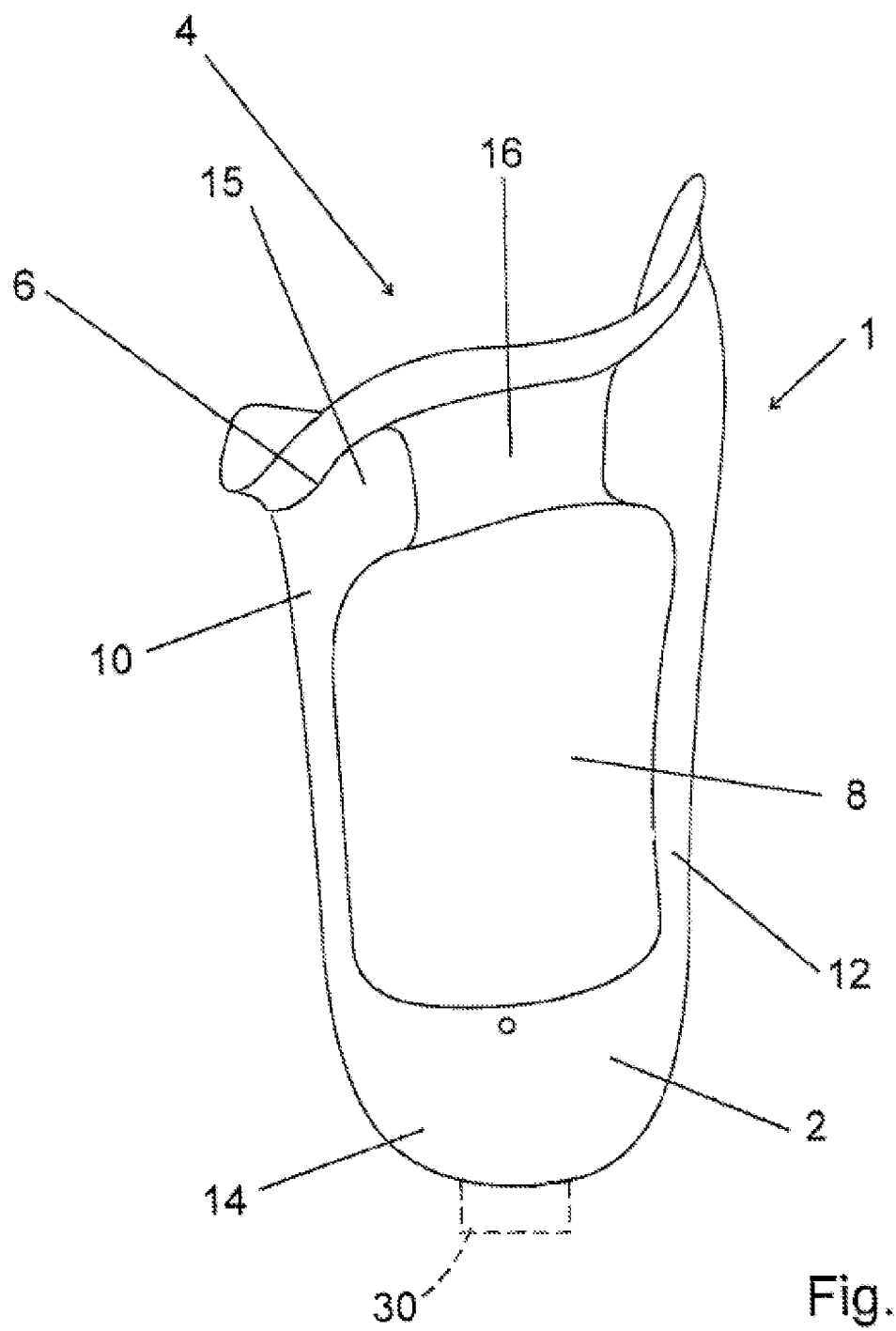
FIG. 1 shows a prosthesis socket according to a first illustrative embodiment of the present invention.

FIG. 1 shows a prosthesis socket 1 according to an illustrative embodiment of the present invention. The prosthesis socket 1 has an outer socket 2, which comprises a proximal opening 4 surrounded by an outer-socket edge 6. In the inside of the outer socket 2, there is an inner socket 8 which, in the proximal direction, i.e. upward in FIG. 1, protrudes beyond the outer-socket edge 6 and delimits the prosthesis socket 1 in the proximal direction.

The outer socket 2 is made of a rigid material, for example a fiber-reinforced plastic. This can be, for example, a carbon fiber composite, i.e. a carbon-fiber-reinforced plastic. By means of the inner socket 8 protruding above the outer-socket edge 6 in the proximal direction, the hard and rigid outer-socket edge 6 is padded for the wearer of the prosthesis or of the prosthesis socket 1.

It will be seen that the outer socket 2 has a medial part 10 and a lateral part 12, which are connected to each other at a distal end 14 of the outer socket 2. In the proximal region, the medial part 10 and the lateral part 12 are connected by a flexible and non-elastic material 16. The latter is located, as is shown in FIG. 1, in a ventral region of the outer socket 2. A proximal part 15 of the medial part 10 comprises ca. ⅓ of the ventral surface in a rigid and non-elastic configuration, since it is made of the rigid material of the outer socket 2. This configuration, for example from carbon-fiber-reinforced plastic, ensures the controllability and the secure fixing on the amputation stump. In addition, an in particular permanent deformation of the flexible and non-elastic material 16 in the ventral region is prevented.

As an alternative to the embodiment shown in FIG. 1, it is also possible, for example, for the region between the medial part 10 and the lateral part 12 to be filled completely with the flexible and non-elastic material 16. This would have the advantage of preventing the inner socket 8, with the amputation stump located therein, from bulging out of the window formed between the medial part 10 and the lateral part 12. However, the embodiment shown in FIG. 1 greatly improves the sensorimotor capacity, i.e. the perception of the environment, via the amputation stump. If the inner socket 8 is also made of a silicone, for example an HTV silicone, its breathability is greatly improved and, in addition, a restriction of the function of the musculature of the amputation stump is reduced. The elasticity of the silicone is limited by incorporation of a woven fabric.

Figure 2:
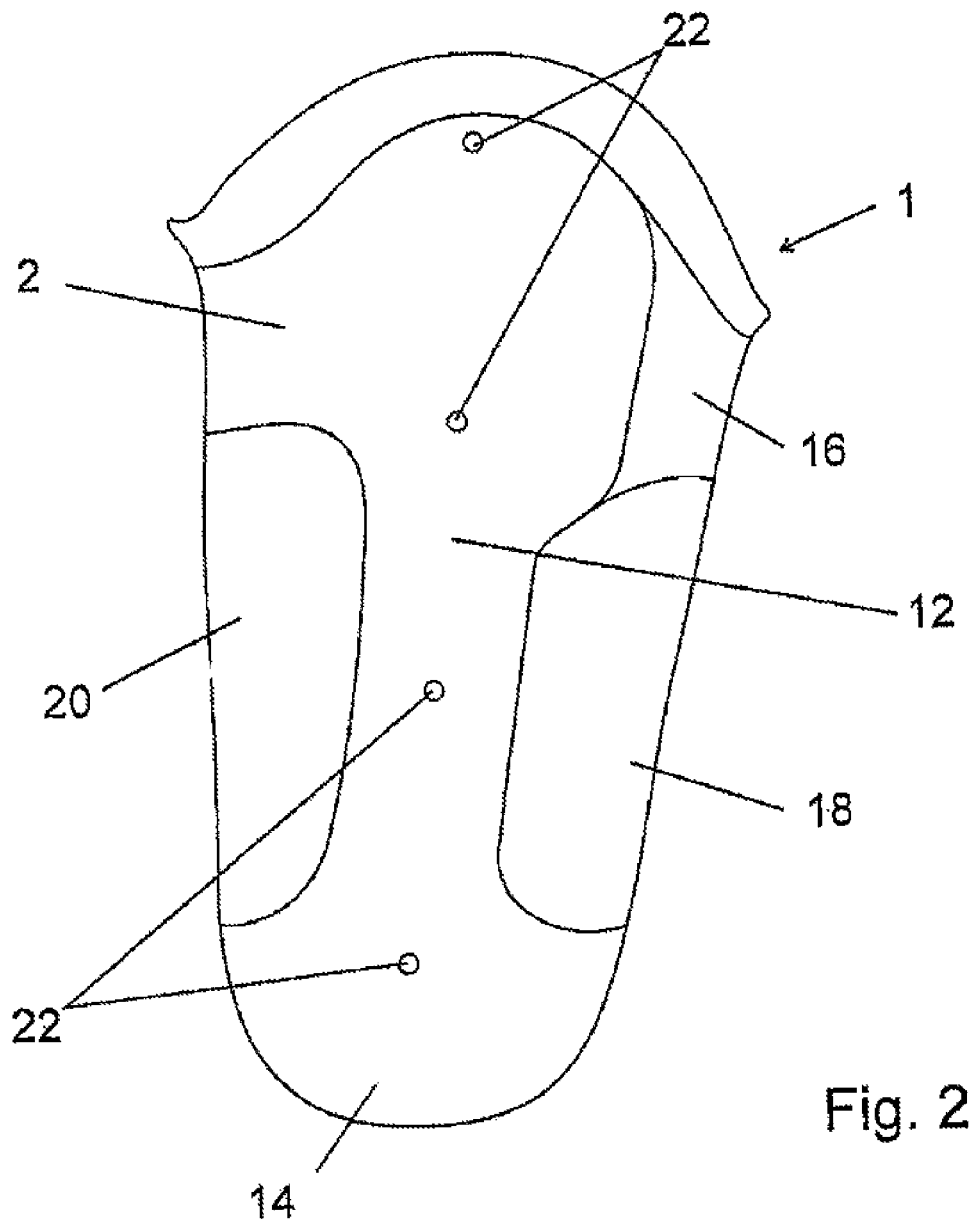
FIG. 2 shows a prosthesis socket according to an illustrative embodiment of the present invention.

FIG. 2 shows the prosthesis socket 1 from FIG. 1 in a side view. The lateral part 12 of the outer socket 2 and the distal end 14 thereof can thus be seen. It will also be noted that, in addition to the outer socket 2 being provided with a ventral window 18 limited at the top by the flexible and non-elastic material 16, a dorsal window 20 is also present in the dorsal region, i.e. to the rear. Particularly when sitting down while wearing the depicted prosthesis socket 1, this leads to much improved perception of the environment via the prosthesis socket.

In the lateral part 12, several bores 22 are also shown through which connecting elements, for example screw connectors, can be guided in order to connect the outer socket 2 to the inner socket in a manner free of pistoning.

Figure 3:
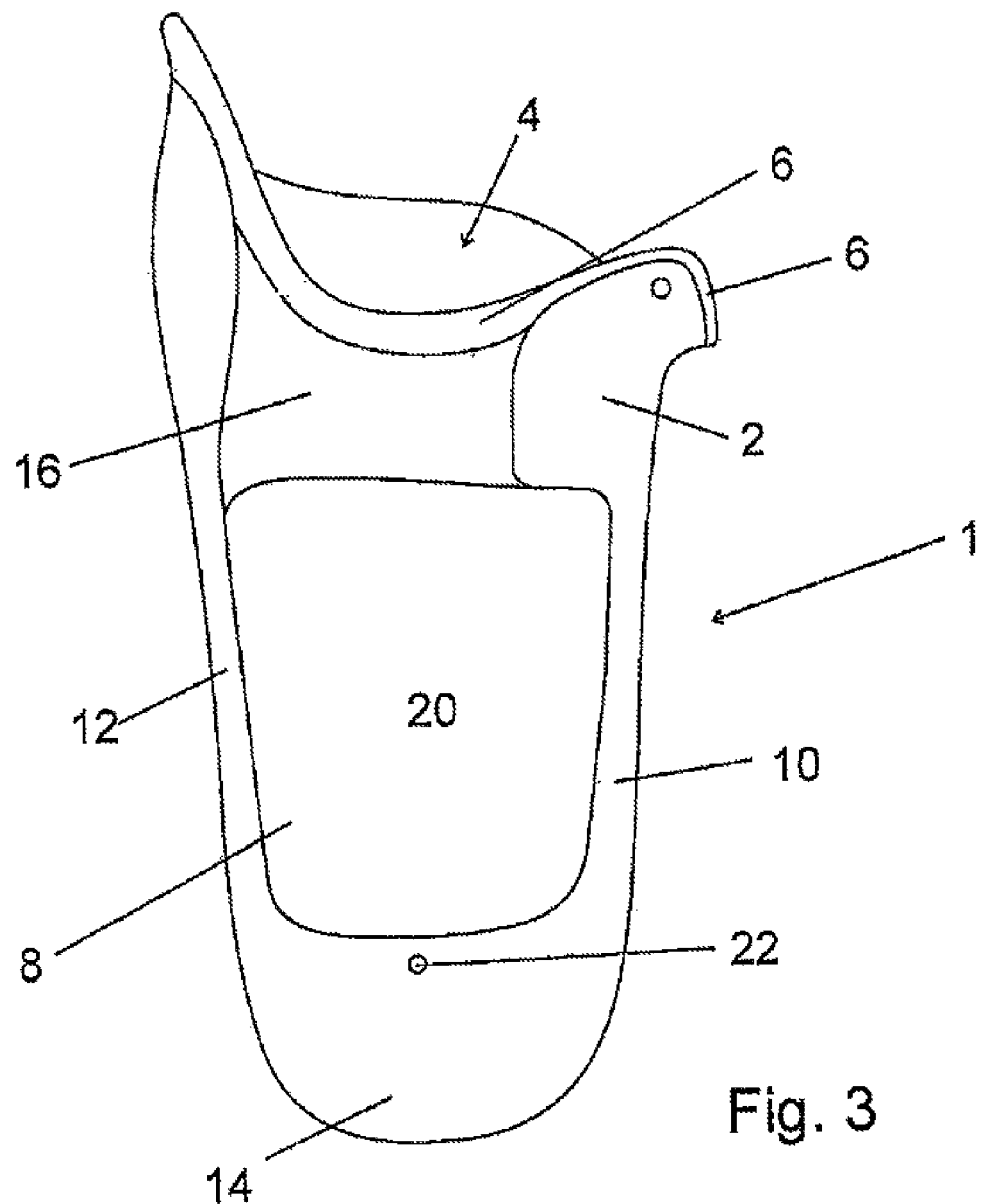
FIG. 3 shows a prosthesis socket according to a further illustrative embodiment of the present invention.

FIG. 3 shows the prosthesis socket 1 in a dorsal view. This shows the dorsal window 20 in the outer socket 2, through which the inner socket 8 can be seen. FIG. 3 also shows that an insert made of the flexible and non-elastic material 16 is also located on the dorsal face, i.e. to the rear, between the medial part 10 and the lateral part 12. This insert ensures a much more comfortable feel, particularly when sitting down while wearing such a prosthesis socket 1, since, on the one hand, it yields to the loads that occur and it deforms accordingly to the forces that occur and thus leads to much fewer pressure sores, and, on the other hand, it permits a perception of the environment that would not be possible through a rigid material. At the distal end 14 of the prosthesis socket 1 shown in FIG. 1, there is a connecting member 30 for securing a distal prosthetic device here to the prosthesis socket 1.

Figure 4:
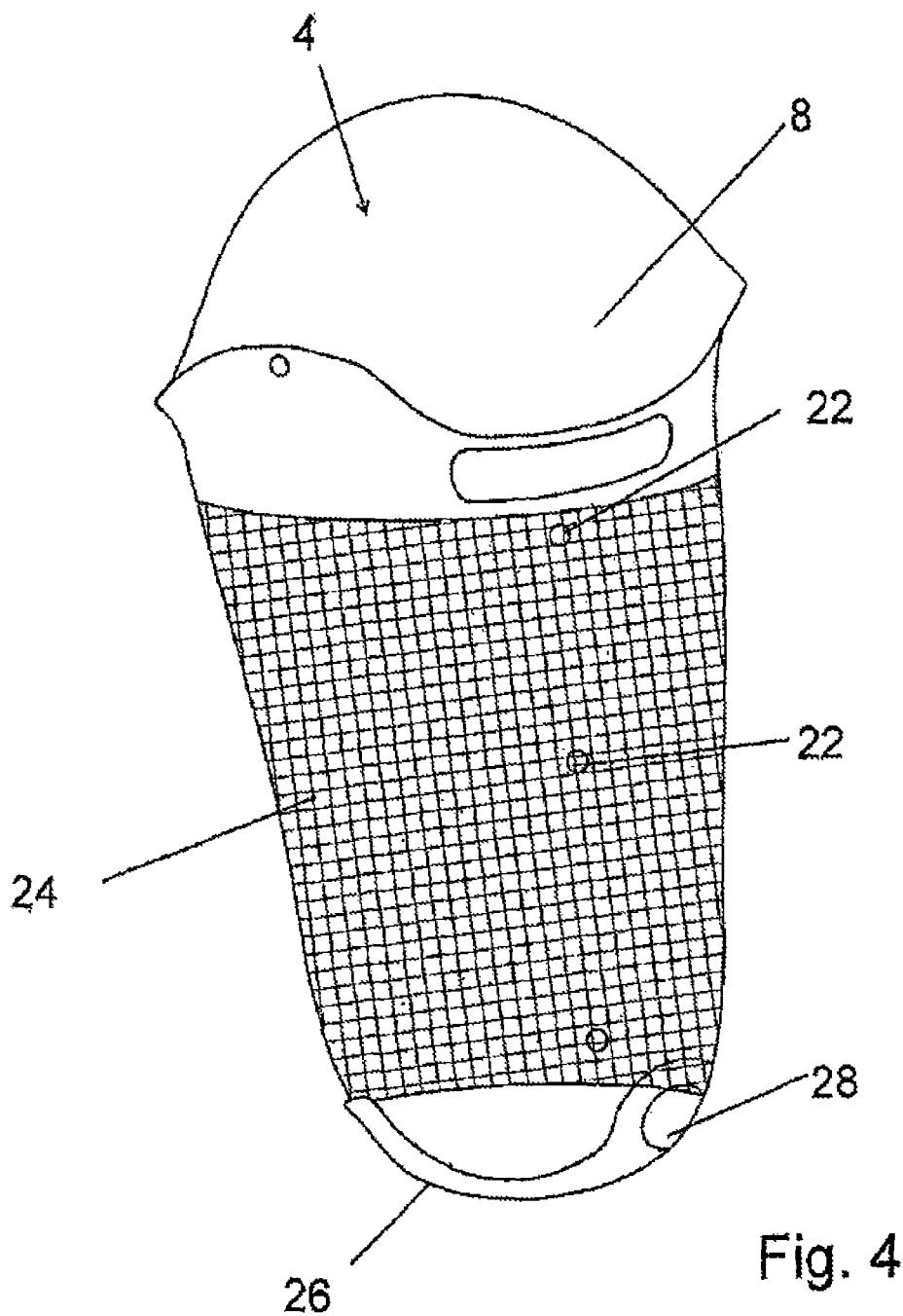
FIG. 4 shows an inner socket for a prosthesis socket according to an illustrative embodiment of the present invention.

FIG. 4 shows the inner socket 8 for the prosthesis socket 1 from FIGS. 1 to 3. The inner socket 8 also has a proximal opening 4, which is provided for receiving the amputation stump. The inner socket 8 is made of a flexible and cushioning material, for example one or more layers of silicone. By way of bores 22, which are adapted to the position of the bores 22 in the outer socket 2 as shown in FIG. 2, the outer socket 6 can be connected to the inner socket 8 in a manner free of pistoning. In the middle region of the inner socket 8, a bistable matrix 24 can be seen, which is indicated by intersecting lines. This bistable matrix 24 suppresses the elasticity of the inner socket 8 in this region. Since the outer socket 2 has its ventral window 18 and/or its dorsal window 20 in this region, too great an elasticity of the inner socket 8 in this region can result in the inner socket 8, with the amputation stump located therein, bulging out. The bistable matrix 24 reliably prevents this and therefore, on the one hand, the hold of the prosthesis socket 1 on the amputation stump is improved and, on the other hand, the wearing comfort is enhanced.

In the distal region, the inner socket 8 shown in FIG. 4 has a distal buckle 26 made of a rigid solid material which, for example, can be the same fiber-reinforced plastic of which the outer socket 2 is also made. This distal buckle 26 prevents a collapse of the distal end of the inner socket 8 and at the same time offers a hold for a valve, which can be fitted into a valve opening 28 provided for this purpose. This can be, for example, a conventional outlet valve through which any air located between the inner socket 8 and the amputation stump is pumped out as a result of the pumping movement that occurs when walking with the prosthesis socket 1. In this way, an underpressure between the inner socket 8 and the amputation stump is maintained, thus resulting in a firm connection between the amputation stump and the prosthesis socket 1.

Figure 5:
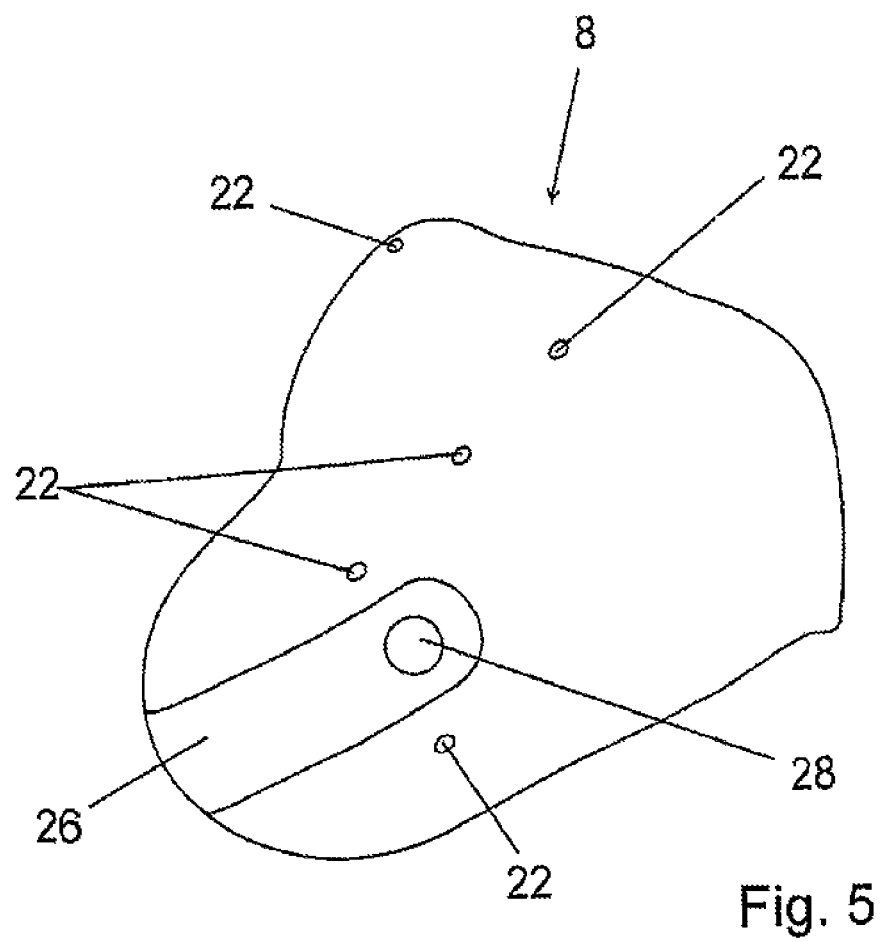
FIG. 5 shows the inner socket from FIG. 4 from another angle.

FIG. 5 shows the inner socket 8 from a slightly different perspective. It shows a plurality of bores 22 into which, for example, it is possible to fit locking nuts, which interact with screws inserted into the bores 22 in the outer socket 2 and thus connect the inner socket 8 to the outer socket 2 in a manner free of pistoning. The distal buckle 26, with the valve opening 28 provided therein, is once again shown in the distal region of the inner socket 8. For reasons of clarity, the bistable matrix 24 has not been depicted again.

In a preferred embodiment, the inner socket 8 has, on its inside face, a sliding inner coating, which can be applied by means of a CVD method, for example. This avoids friction and associated skin irritation between the proximal end of the prosthesis socket 1, which is formed by the inner socket 8, and the skin of the patient. A sliding coating on the outside face of the inner socket 8 is expedient particularly in the proximal part of the inner socket 8 that protrudes past the outer-socket edge 6 in the proximal direction. This prevents friction and adhesion between the inner socket 8 and the patient's clothing. At the same time, a sliding coating on the inside face of the inner socket 8 makes it much easier for the patient to get into the prosthesis socket 1.

LIST OF REFERENCE SIGNS 1 prosthesis socket
2 outer socket
4 proximal opening
6 outer-socket edge
8 inner socket
10 medial part
12 lateral part
14 distal end
15 proximal region
16 flexible and non-elastic material
18 ventral window
20 dorsal window
22 bore
24 bistable matrix
26 distal buckle
28 valve opening

The invention claimed is:

1. A prosthesis socket for a prosthesis, the prosthetic socket comprising:
   an attachment member adapted to be connected to a distal prosthetic device;
   an outer socket which is formed mainly from a rigid material and comprises a closed distal end, a ventral window, and a proximal opening configured to receive an amputation stump, said proximal opening being surrounded by an outer-socket edge and a flexible material, the flexible material extending between two rigid portions of the outer socket in a ventral region of the amputation stump, the flexible material being adapted to a body shape of a wearer of the prosthesis socket without the proximal opening widening, the flexible material comprising a fiber-reinforced plastic, the flexible material having a rest position that matches an expected body shape of the wearer and is a position the flexible material returns to when not subjected to forces, the outer socket being shaped to at least partially conform to the amputation stump, the ventral window having outer limits consisting of the outer-socket edge and the flexible material;
   an inner socket positioned inside the outer socket and extending proximal of the outer-socket edge, the inner socket comprising a flexible material.

2. The prosthesis socket as claimed in claim 1, wherein the rigid material comprises a fiber-reinforced plastic.

3. The prosthesis socket as claimed in claim 2, wherein the rigid material and the flexible material comprise the same plastic.

4. The prosthesis socket as claimed in claim 1, wherein the outer-socket edge is formed from the flexible material in a dorsal region.

5. The prosthesis socket as claimed in claim 4, wherein the flexible material in the dorsal region of the outer-socket edge is the same material as the flexible material in the ventral region of the outer-socket edge.

6. The prosthesis socket as claimed in claim 1, wherein the outer socket is interrupted at least one place.

7. The prosthesis socket as claimed in claim 1, wherein the inner socket is connected to the outer socket in a manner free of pistoning.

8. The prosthesis socket as claimed in claim 7, wherein the inner socket is connected to the outer socket by at least one screw connection comprising a distal screw connection.

9. A prosthesis socket, comprising:
- an attachment member adapted to be connected to a distal prosthetic device;
- an outer socket comprising a closed distal end, a ventral window, and a proximal opening for receiving an amputation stump, the outer socket being formed from a rigid material and being shaped to at least partially conform to the amputation stump;
- an outer-socket edge and a flexible material surrounding the proximal opening, the flexible material extending between two rigid portions of the outer socket in a ventral region of the amputation stump, the flexible material being adapted to a shape of the amputation stump without the proximal opening widening, the flexible material comprising a fiber-reinforced plastic, the flexible material having a rest position that matches an expected body shape of the wearer and is a position the flexible material returns to when not subjected to forces, the ventral window having outer limits consisting of the outer-socket edge and the flexible material;
- an inner socket positioned inside the outer socket and extending proximal of the outer-socket edge, the inner socket comprising a flexible material.

10. The prosthesis socket of claim 9, wherein the rigid material comprises a fiber-reinforced plastic.

11. The prosthesis socket of claim 9, wherein the rigid material and the flexible material comprise the same plastic.

12. The prosthesis socket of claim 9, wherein the outer-socket edge is formed from the flexible material in a dorsal region.

13. The prosthesis socket of claim 12, wherein the flexible material in the dorsal region of the outer-socket edge is the same material as the flexible material in the ventral region of the outer-socket edge.

14. The prosthesis socket of claim 9, wherein the outer socket comprises at least one discontinuity.

15. The prosthesis socket of claim 9, wherein the inner socket is connected to the outer socket in a manner free of pistoning.

16. The prosthesis socket of claim 15, wherein the inner socket is connected to the outer socket by at least one distal screw connection.

* * * * *